(12) United States Patent
Erdmann et al.

(10) Patent No.: US 8,076,452 B2
(45) Date of Patent: Dec. 13, 2011

(54) STREPTAVIDIN-BINDING PEPTIDE

(76) Inventors: Volker A. Erdmann, Berlin (DE);
Thorsten Lamla, Berlin (DE)

(*) Notice: Subject to any disclaimer, the term of this patent is extended or adjusted under 35 U.S.C. 154(b) by 799 days.

(21) Appl. No.: 10/506,480

(22) PCT Filed: Feb. 20, 2003

(86) PCT No.: PCT/DE03/00605
§ 371 (c)(1),
(2), (4) Date: Aug. 15, 2005

(87) PCT Pub. No.: WO03/074546
PCT Pub. Date: Sep. 12, 2003

(65) Prior Publication Data
US 2006/0106199 A1    May 18, 2006

(30) Foreign Application Priority Data

Mar. 1, 2002 (DE) .............................. 102 08 877
Oct. 16, 2002 (DE) .............................. 102 48 318

(51) Int. Cl.
*A61K 38/08* (2006.01)
*C07K 14/00* (2006.01)
(52) U.S. Cl. ........................ 530/328; 530/350
(58) Field of Classification Search ................. 530/300, 530/329
See application file for complete search history.

(56) References Cited

U.S. PATENT DOCUMENTS

| | | | | |
|---|---|---|---|---|
| 5,021,347 A | 6/1991 | Yasui et al. | ................. | 435/235.1 |
| 5,506,121 A | 4/1996 | Skerra et al. | ................. | 235/69.7 |
| 6,342,581 B1* | 1/2002 | Rosen et al. | ................. | 530/300 |
| 6,551,795 B1* | 4/2003 | Rubenfield et al. | ........... | 435/69.1 |
| 6,833,447 B1* | 12/2004 | Goldman et al. | ............. | 536/23.1 |

FOREIGN PATENT DOCUMENTS

| | | |
|---|---|---|
| EP | 0312 617 B1 | 4/1989 |
| EP | 0401 369 B1 | 12/1990 |
| EP | 0593 757 B1 | 4/1994 |
| WO | WO 99/57565 | 11/1999 |
| WO | WO 01/01748 | 1/2001 |
| WO | WO 01/90331 A2 | 11/2001 |
| WO | WO 02/38580 | 5/2002 |
| WO | WO 03/048304 | 6/2003 |

OTHER PUBLICATIONS

Yoshida et al. Three asparagine synthetase genes of *Bacillus subtilis*. Journal of Bacteriology. 1999. vol. 181, pp. 6081-6091.*
Yoshioka et. Identification of open reading frames in *Schizosaccharomyces pombe* cDNAs. DNA Research. 1997. vol. 4, pp. 363-369.*
Appendix A—Selected sequence alignments from SCORE.*
Yamaki E.A, "High performance liquid chromatography of peptides on a microspherical carbon column", *Journal of Chromatography A*, 729, 1996, pp. 143-153.
Velazquez C. et al., "Quantitation of Lysozyme Peptides Bound to Class II MHC Molecules Indicates Very Large Differences in Levels of Presentation", *The Journal of Immunology*, 166, 2001, pp. 5488-5494.
Kay B.K. et al., "AN M13 phage library displaying random 38-amino-acid peptides as a source of novel sequence with affinity to selected targets", *Gene*, 128, 1993, pp. 59-65.
Lamla T. et al., "In vitro selection of other proteins than antibodies by means of ribosome display", *FEBS letters*, 502, 2001, pp. 35-40.
Zang X. et al., "Tight-binding streptavidin ligands from a cyclic peptide library", *Bioorganic & Medicinal Chemistry Letters*, 8, 1998, pp. 2327-2332.
Østergaard S. et al., "Novel avidin and streptavidin binding sequences found in synthetic peptide libraries", *FEBS Letters*, 362, 1995, pp. 306-308.
Devlin J.J. et al., "Random Peptide Libraries: A Source of Specific Protein Binding Molecules", *Science*, vol. 249, Jul. 27, 1990, pp. 404-406.
Wilson David S. et al., "The use of mRNA display to select high-affinity protein-binding peptides", PNAS, vol. 98, No. 7, Mar. 27, 2001, pp. 3750-3755.
Lamla T. et al., "Searching Sequence Space for High-affinity Binding Peptides using Ribosome Display", J. Mol. Biol. 329, 2003, pp. 381-388.
Schmidt T.G.M. et al., "Molecular Interaction Between the Strep-tag affinity Peptide and its Cognate Target, Streptavidin", J. Mol. Biol. 255, 1996, pp. 753-766.
GenBank AAB90424 http://www.ncbi.nlm.nih.gov/entrez/viewer.fcgi?2649790:OLD12:450184.
GenBank BAB49397 http://www.ncbi.nlm.nih.gov/entrez/viewer.fcgi?db=protein&val=14022789.
GenBank CAB50185 http://www.ncbi.nlm.nih.gov/entrez/viewer.fcgi?db=protein&val=5458698.

* cited by examiner

*Primary Examiner* — Suzanne M. Noakes

(57) ABSTRACT

The invention relates to novel streptavidin binding peptides.

1 Claim, 2 Drawing Sheets

US 8,076,452 B2

STREPTAVIDIN-BINDING PEPTIDE

FIELD OF THE INVENTION

The invention relates to a streptavidin-binding peptide and to methods for the production of a streptavidin-binding peptide in a cell-based or cell-free protein biosynthesis system. Further, the invention relates to the use of a streptavidin-binding peptide for purifying a defined protein produced in a protein biosynthesis system, and to the use of a streptavidin-binding peptide for marking a defined protein.

PRIOR ART

Methods for efficiently expressing defined proteins in various pro- and eukaryotic organisms are known in the art and do not require further explanations. As defined proteins are understood here peptides and/or proteins, which are expressed naturally or after transformation or use of defined RNA in the organism used for the expression or cell-free expression system and are enriched in purification steps.

Methods for the cell-free expression of defined proteins are, for instance, known in the art from documents EP 0312 617 B1, EP 0401 369 B1 and EP 0593 757 B1. According thereto, the components necessary for transcription and/or translation are incubated, in addition to a nucleic acid strand coding for a defined protein, in a reaction vessel and after the expression the polypeptides/proteins are isolated from the reaction solution. The components necessary for transcription as well as for translation can be obtained from the supernatants of pro- or eukaryotic cell lysates after centrifugation.

An essential problem for the expression of defined proteins in pro- and eukaryotic organisms and for the cell-free expression is the purification and/or the detection of the expressed defined proteins. This is particularly problematic with defined proteins, for which there are no antisera or monoclonal antibodies. For simplifying the purification and the detection of such defined proteins, they are expressed as so-called fusion proteins. Hereby, an amino acid sequence is added N- and/or C-terminally to the defined protein or inserted between two protein domains (internally), the fusion partner. This happens on the nucleic acid level, so that the defined protein as well as the fusion partner added for the detection and/or purification are expressed together during a transcription/translation process as a chimeric (fusion) protein, consisting of the defined protein and the fusion partner. The mentioned fusion partner may be a single amino acid, but also a peptide or protein. For these added fusion partners, there are available binding partners immobilized for purification, and the fusion proteins can be isolated with these binding partners. In addition to the possibility of the purification of the proteins, they may also be detected with binding partners being specific for the fusion partner. These binding partners may be antibodies specific for the fusion partner or also other proteins, peptides or chemical compounds specifically binding to the fusion partner.

Examples for such fusion partners are the Myc-tag (Munro & Pelham, Cell 46:291-300, 1986; Ward et al., Nature 341:544-546, 1998), the FLAG peptide (Hopp et al., Bio/Technology 6:1204-1210, 1988), the KT3 epitope peptide (Martinet et al., Cell 63:843-849, 1990; Martin et al., Science 255:192-194, 1992) and the alpha-tubulin epitope peptide (Skinner et al., J. Biol. Chem. 266:14163-14166, 1991), all of which were successfully used for the detection and in part also for the purification of proteins. For part of the fusion partners normally having a length of 3 to 12 amino acids, it could be shown that they do not affect the biological function of the defined proteins. The biological function of the defined protein is, however, affected with increasing length of the fusion partner, since the additionally expressed amino acids can affect e.g. the development of the secondary, tertiary and/or quaternary structure. Longer fusion partners are thus suitable for the detection of the proteins, but less for the purification of the proteins. On the other hand, longer fusion partners frequently have a higher affinity with their specific binding partners.

A substantial drawback of the above fusion partners with respect to the purification is that the binding to the binding partner is based on an antigen/antibody binding, and the production and purification of the antibodies used as binding partners is time-consuming and expensive. Another drawback is that the antigen/antibody binding requires a very strong binding between the binding partner, e.g. antibody immobilized at a matrix, and the fusion partner. This has as a consequence that for the elution of the fusion protein bound via the fusion partner, sometimes extremely "unphysiological" conditions with respect to the defined protein, are generated. Unphysiological conditions are, e.g., very high or extremely low salt concentrations, use of chaotropic salts and pH values differing by far from the natural pH value of the defined protein. This may affect, under certain circumstances, the structure and/or the functionality of the defined protein or irreversibly destroy it. Correspondingly, the purification of the defined proteins should take place under as "gentle" and physiologic conditions as possible, in order to maintain the functionality of the proteins. For three of the above fusion partners (Hopp et al., 1988; Martin et al., 1990; Skinner et al., 1991), an elution could even be achieved under gentle conditions by means of competitive peptides, however there is still the problem of the time-consuming and expensive antibodies to be purified (and serving as binding partners) and the binding thereof to the matrix.

Further fusion partners consisting of 8 to 9 amino acids are known in the art from the documents U.S. Pat. No. 5,506,121 and Schmidt & Skerra (Protein Engineering, vol. 6, no. 1, 109-122, 1993). The fusion partners disclosed therein are capable of binding to the streptavidin or to the "core" streptavidin, a proteolytically cleaved product of the streptavidin (Bayer et al., Biochem. J. 259:369-376, 1989).

All known Fusion partners that bind to the streptavidin containing the amino acid sequence HPQ, the so-called HPQ binding motif coming into interaction with the biotin-binding pocket of the streptavidin. To the already known peptides belong the so-called Strep-tag I: AWRHPQFGG [SEQ ID NO: 18] with a dissociation constant of Kd of 10-37 µM, the so-called Strep-tag II: WSHPQFEK [SEQ ID NO: 19] with a dissociation constant Kd of 18-72 µM, and the so-called SBP-tag: MDEKTTGWRGGHVVEGLAGELEQLRAR-LEHH PQGQREP [SEQ ID NO: 20] with a dissociation constant Kd of 2.5 nM. In contrast to the two short Strep-tags I and II, the longer SBP-tag has a substantially stronger binding to the streptavidin. However, as mentioned above, the function of the defined protein is particularly affected with increasing length of the fusion partner. Further, particularly long fusion partners disturb the crystallization of the defined proteins.

TECHNICAL OBJECT OF THE INVENTION

It is the technical object of the invention to provide a streptavidin-binding peptide that is as short as possible yet still has a strong binding affinity to streptavidin.

BASICS OF THE INVENTION AND PREFERRED EMBODIMENTS

Figure 1:
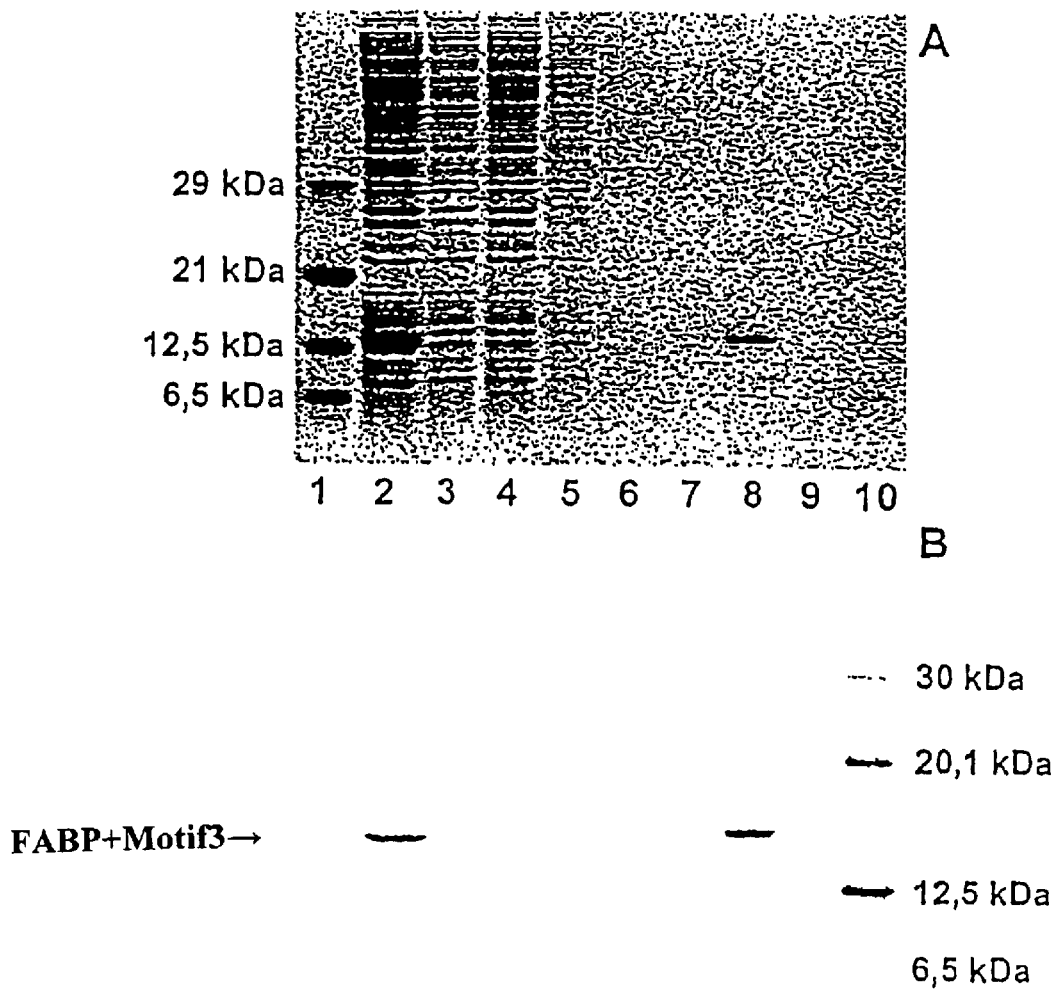
FIG. 1 is a schematic representation of a SDS polyacrylamide electrophoresis gel showing the result of purification of FABP with streptavidin-binding peptide according to motif 3 as a fusion partner after cell-free protein biosynthesis via a streptavidin affinity column.

For achieving the technical object, the invention relates to a streptavidin-binding peptide comprising or consisting of an amino acid sequence according to SEQ ID NOS: 1-12. By the streptavidin-binding peptide according to the invention comprising an amino acid sequence according to SEQ ID NOS: 1-12 it is achieved, compared to prior art, a substantially stronger binding between the streptavidin-binding peptide and the streptavidin, or the streptavidin-binding peptide can substantially be shorter with the same binding strength.

Further, the invention relates to a nucleic acid coding for a streptavidin-binding peptide according to SEQ ID NOS: 1-12 and a plasmid comprising a nucleic acid according to the invention. It is understood that the nucleic acid coding for a streptavidin-binding peptide according to the invention and/or the plasmid can be adjusted to the respective expression system/protein biosynthesis system. The plasmid may be adapted as an expression vector, in particular for bacteria, comprising a region with at least one interface for a restriction enzyme, in which the nucleic acid sequence coding for a defined protein may be inserted, and thus the defined protein is expressed together with the streptavidin-binding peptide according to SEQ ID NOS: 1-12. It is understood that the region coding for the defined protein and for the streptavidin-binding peptide according to SEQ ID NOS: 1-12 are under the control of a suitable promoter and/or operator and terminator. The region with at least one interface for at least one restriction enzyme may lie in the 5' as well as 3' direction of the nucleic acid region coding for the streptavidin-binding peptide according to SEQ ID NOS: 1-12. The nucleic acid region coding for the streptavidin-binding peptide according to SEQ ID NOS: 1-12 needs not to follow immediately to the nucleic acid region coding for the defined protein, rather there may be nucleic acids coding for 1 to 20 amino acids, in particular for 5 to 10 amino acids, between the two regions.

The invention also relates to a method for the production of a streptavidin-binding peptide according to SEQ ID NOS: 1-12, wherein a nucleic acid is expressed or overexpressed in a cell-based or cell-free protein biosynthesis system. The thus produced peptide can easily be isolated via the binding to the streptavidin. The obtained translation product, i.e. a streptavidin-binding peptide according to SEQ ID NOS: 1-12, is contacted with immobilized streptavidin and is bound thereto. After separation of the solution with substances not bound to streptavidin, the translation product is eluted. As an elution agent, buffers can be used, which contain biotin or related substances and/or derivatives, such as iminobiotin, desthiobiotin and/or diaminobiotin. The obtained streptavidin-binding peptide according to SEQ ID NOS: 1-12 carries in the case of the fusion with the defined protein this protein. It may also be used independently from a defined protein for the antibody production. The obtained antibodies can be used e.g. for the detection or purification of the streptavidin-binding peptides according to SEQ ID NOS: 1-12 or in the case that the streptavidin-binding peptide according to SEQ ID NOS: 1-12 is employed as a fusion partner, of the defined protein bound to this fusion partner.

It is understood that the production of such a streptavidin-binding peptide containing an amino acid sequence according to SEQ ID NOS: 1-12 is also possible by means of chemical solid phase synthesis, for instance with an automatic synthesis system made by Abimed (Langenfeld, Germany). This method is based on the standard protocols of the Fmoc chemistry (Fmoc=9-fluorenylmethyloxycarbonyl).

The invention also relates to the use of a streptavidin-binding peptide according to SEQ ID NOS: 1-12 for the purification of a defined protein produced in a protein biosynthesis system, wherein a nucleic acid coding for the protein and, connected therewith, for the streptavidin-binding peptide is subjected to a transcription and/or translation, wherein a solution comprising the thus obtained translation product is contacted with immobilized streptavidin and is bound thereto, and wherein after separation of the solution with substances not bound to streptavidin the translation product is eluted. The elution may take place under gentle conditions for the defined protein. As an elution agent, buffers can be used, which contain biotin or related substances and/or derivatives, such as iminobiotin, desthiobiotin and/or diaminobiotin. The produced defined protein may comprise, N and/or C terminally, the streptavidin-binding peptide according to SEQ ID NOS: 1-12 serving as a fusion partner.

If a streptavidin-Sepharose column is used, the defined protein to be investigated can be immobilized at the matrix by means of the streptavidin-binding peptide according to SEQ ID NOS: 1-12 serving as a fusion partner and isolated from a mixture of molecules, e.g. a cell lysate.

The invention also relates to the use of a streptavidin-binding peptide according to SEQ ID NOS: 1-12 for labeling a defined protein, wherein a nucleic acid coding for the protein and, connected therewith, for the streptavidin-binding peptide is subjected to transcription and/or translation, wherein the thus obtained translation product is contacted with a streptavidin conjugate comprising a reporter molecule and bound thereto. The labeled defined protein may comprise, N and/or C terminally, the streptavidin-binding peptide according to SEQ ID NOS: 1-12 serving for labeling. Reporter molecules may, for instance, be radioactive and/or radioactively labeled substances. It is understood that the streptavidin as such may also be radioactive and/or radioactively labeled; in this case a reporter molecule is not needed. Reporter molecules may also be fluorescent substances or enzymes, such as alkaline phosphatase or peroxidase. Such streptavidin compounds coupled to a reporter molecule, for instance proteins, which have the streptavidin-binding peptide according to SEQ ID NOS: 1-12 as a fusion partner, can be detected and/or quantified on a Western blot or in the ELISA (enzyme linked immunosorbent assay). If the defined proteins are binding proteins, other proteins binding thereto can also be detected in this way. Binding proteins are in this context proteins, which themselves bind other proteins and/or themselves bind to other proteins, such as in an antigen/antibody binding or in a binding of a protein to a receptor.

Preferred is a streptavidin-binding peptide comprising less than 30 amino acids, preferably less than 20 amino acids, most preferably less than 10 amino acids.

In the following, the invention is explained in more detail, based on figures and examples representing embodiments only.

FIG. 1: purification of FABP with streptavidin-binding peptide according to motif 3 as a fusion partner after cell-free protein biosynthesis via a streptavidin affinity column. A comparable amount of each fraction was analyzed by means of SDS polyacrylamide gel electrophoresis. (A) Coomassie stained and (B) autoradiogramme. The samples in the numbered tracks are (1) molecular weight markers; (2) reaction mixture; (3) passage of the sample application; (4-6) washing fractions; (7-9) elution fractions; (10) radioactive molecular weight marker.

Figure 2:
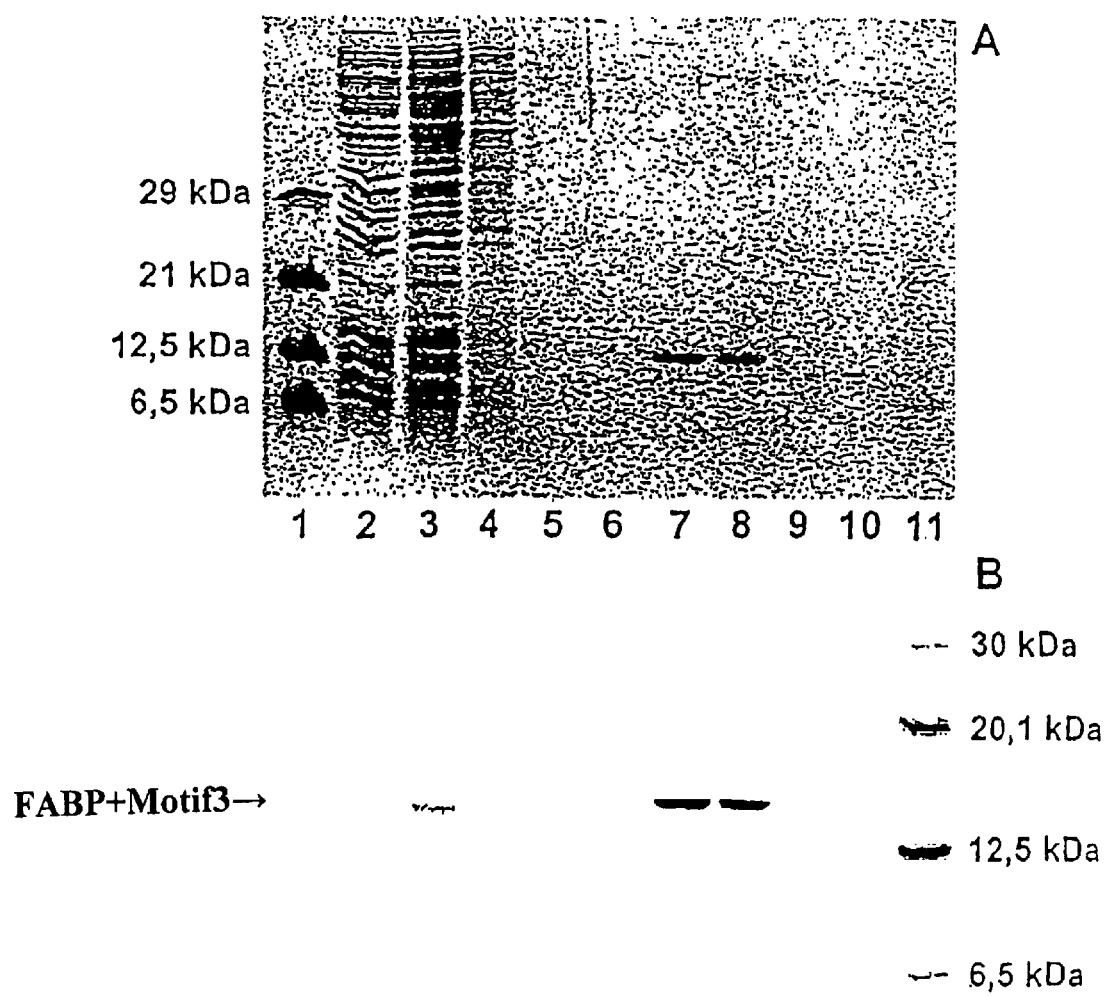
FIG. 2 is a schematic representation of a SDS polyacrylamide electrophoresis gel showing the result of purification of FABP with streptavidin-binding peptide according to motif 3 as a fusion partner after cell-free protein biosynthesis via a StrepTactin affinity column.

FIG. 2: purification of FABP with streptavidin-binding peptide according to motif 3 as a fusion partner after cell-free protein biosynthesis via a StrepTactin affinity column. A comparable amount of each fraction was analyzed by means of SDS polyacrylamide gel electrophoresis. (A) Coomassie stained and (B) autoradiogramme. The samples in the numbered tracks are (1) molecular weight markers; (2) passage of the sample application; (3-5) washing fractions; (6-10) elution fractions; (11) radioactive molecular weight marker.

Example 1

Binding Peptides According to the Invention and Comparison Peptides with Dissociation Constants Using standard methods for this technology, the FAB protein (fatty acid binding protein) (FABP) from bovine hearts was expressed in vitro in a cell-free protein biosynthesis by means of a coupled transcription/translation system. The expressed FAB protein had at the N terminus an additional streptavidin-binding peptide composed of 15 amino acids with different amino acid sequences as fusion partners.

Two binding peptides contain in their amino acid sequence the HPQ motif (motif 1 and 2) described in the prior art, and two of them contain the streptavidin-binding peptide according to SEQ ID NOS: 1-6 according to the invention (motif 3 and 4). The sequences of the peptides are shown in Table 1. In addition, the expressed proteins were provided at the C terminus with a "His-tag" consisting of 6 histidines. The proteins were purified by means of affinity chromatography via Ni2+IDA-agarose using standard methods. It can be seen that with equal length, binding peptides of a sequence according to the invention have a substantially lower dissociation constant than a binding peptide with HPQ motif. The Kd value of a binding peptide according to the invention is in the order of the SBP-tag in spite of the 2.5 fold length of the SBP-tag.

TABLE 1

| Sequence | | Dissociation constant [kd] |
|---|---|---|
| motif 1 | D L Y D I D R N W V G H-P Q G<br>SEQ ID NO: 14 | 8 μM |
| motif 2 | D N Y D A D L A W D T H-P Q D<br>SEQ ID NO: 15 | 70 μM |
| motif 3 | D V E A W L D E R V P L-V E T<br>SEQ ID NO: 16 | 84 nM |
| motif 4 | D V E A W I A D P A V H-F T T<br>SEQ ID NO: 17 | 200 nM |

Example 2

Kind of Measurement of the Dissociation Constant of Table 1

The measurements of the dissociation constant were performed with a BiacoreX system and the sensor chip NTA of the company Biacore. The proteins generated during the expression described in Example 1 were investigated, i.e. FAB proteins, which had at the N terminus a peptide consisting of 15 amino acids as fusion partners and at the C terminus 6 histidines, which were needed for the immobilization on the sensor chip. The binding affinity of the proteins generated during the expression to streptavidin described in Example 1 was measured in the Biacore device according to manufacturer's instructions. The protein to be investigated is on the sensor chip, and a streptavidin solution having a defined concentration is sprayed in. The interaction (binding) between the two molecules is measured by the device and quantified as so-called resonance units (RU). For the measurement, the buffers specified by the manufacturer were used.

The results of the measurements are shown in Table 2. The obtained measurements were evaluated with the provided software and led to the dissociation constants shown in Table 1.

TABLE 2

| Motif<br>Streptavidin conc. | 1<br>RU | 2<br>RU | 3<br>RU | 4<br>RU |
|---|---|---|---|---|
| 15 nM  |     |     | 98  |     |
| 30 nM  |     |     | 242 | 68  |
| 60 nM  |     |     | 461 | 171 |
| 125 nM |     |     | 613 | 280 |
| 250 nM |     |     | 704 | 384 |
| 500 nM | 62  |     | 786 | 478 |
| 1 μM   | 123 |     | —   | 560 |
| 2 μM   | 233 |     | 946 | 644 |
| 3 μM   | —   | 64  | —   |     |
| 4 μM   | 407 | —   | 983 |     |
| 6 μM   | —   | 98  |     |     |
| 8 μM   | 621 | —   |     |     |
| 15 μM  | —   | 201 |     |     |
| 16 μM  | 779 | —   |     |     |
| 30 μM  | —   | 337 |     |     |
| 32 μM  | 955 | —   |     |     |
| 60 μM  |     | 536 |     |     |

Example 3

Purification of a Fusion Protein

Using standard methods, the FAB protein having at the N terminus an additional peptide consisting of 15 amino acids with the amino acid sequence DVEAWLDERVPLVET [SEQ ID NO: 16] (motif 3) as fusion partners, is expressed in vitro in a cell-free protein biosynthesis by means of a coupled transcription/translation system. For purification of the overexpressed defined protein, the streptavidin was coupled to a solid phase. As a solid phase was used a Sepharose. The expressed FAB protein was then purified using standard methods via a column comprising streptavidin-Sepharose or StrepTactin-Sepharose. For the purification the following buffers were used: washing buffer (100 mM Tris-HCl (pH 8.0), 150 mM NaCl, 1 mM EDTA).

For the elution of streptavidin, the washing buffer contained 2 mM biotin, and for the elution of StrepTactin, the washing buffer contained 2.5 mM desthiobiotin.

The percentage distribution of the used defined protein on the various fractions of the affinity chromatography can be taken from Table 3. In Table 3, D represents the application of sample/passage, W washing fraction, and E elution fraction.

TABLE 3

| | Fraction | | | | | | | | |
|---|---|---|---|---|---|---|---|---|---|
| | D | W1 | W2 | W3 | E1 | E2 | E3 | E4 | E5 | Tot. |
| Streptavidin | 3.5% | 6.8% | 1.0% | 0.3% | 0.4% | 76.9% | 0.7% | — | — | 89.6% |
| StrepTactin | 3.0% | 7.4% | 1.8% | 0.9% | 0.9% | 45.9% | 23.2% | 1.0% | 0.3% | 84.4% |

When using streptavidin-Sepharose, 90% of the applied protein could be recovered from the column, 78% for the eluate. The quality of the purification is shown in FIG. 1.

When using StrepTactin-Sepharose, 84% of the applied protein could be recovered from the column, 71% for the eluate. The quality of the purification is shown in FIG. 2.

Example 4

Optimization of Individual Binding Peptides

The binding peptide (FAx 3) with the sequence DVEAWLDERVPLVET [SEQ ID NO: 16] was subjected to a substitution analysis, and it was intended thereby to identify a possible minimum motif (=shortened peptide) and examine the effect of individual amino acid exchanges on the binding specificity. In a substitution analysis, peptides are synthesized by means of spot methods (Frank, R. 1992) on a cellulose membrane serving as a solid phase. Every position of the peptide comprising 15 amino acids was systematically replaced by the other 19 L amino acids.

The substitution analysis was incubated with a peroxidase-labeled streptavidin and developed with a luminescence substrate. Thereby it was possible to find out, how far the peptide can be shortened and which amino acids are "conserved" and thus not or only very poorly exchangeable. The following picture resulted: a peptide, which has sufficient streptavidin binding, is the 6-mer peptide DVEAWL [SEQ ID NO: 16]. A clearly better streptavidin binding has the 9-mer peptide DVEAWLDER [SEQ ID NO: 16]. The substitution analysis also indicated positions, where the exchange of the original amino acid by another one could result in an improvement of the streptavidin binding.

The information supplied by the substitution analysis was verified by determining the binding constants of different peptides by surface plasmon resonance spectroscopy using a BIAcore device. The measurements were made with the NTA sensor chip of the company BIAcore and by means of the fatty acid-binding protein from bovine hearts (FABP). The FABP served for the immobilization and presentation of the peptide. Further, it was intended to thus simulate the conditions occurring in an affinity chromatography, since the peptide is to be used in the future as an affinity peptide for the purification of proteins. In contrast to the first measurements, where the peptides to be verified replaced the four N terminal amino acids of the FABP, the arrangement of the peptides was this time also N terminal, but they were not part of the FABP. The His-tag necessary for the immobilization was also modified. It was located same as for the first measurements at the C terminus of the FABP, was however extended from six to eight histidines and further spaced by a linker consisting of two glycines from the FABP. Thereby, the immobilization of the ligands could distinctly be improved, and thus the drift of the base line resulting from the washing-off of the ligand could be minimized. For every measurement, an identical amount of the respective FABPs was immobilized, what corresponded to a rise of the base line by 1,100 resonance units (RU). As a reference was used the FABP with the His-tag, but without N terminal binding peptide.

The binding constants obtained with the optimized measuring method were the following:

| | Kd |
|---|---|
| Peptide (FAx 3): | |
| D V E A W L D E R V P L V E T SEQ ID NO: 16 (AspValGluAlaTrpLeuAspGluArgValProLeuValGluThr) | 3.6 ± 0.6 nM |
| Shortened peptide (9-mer): DVEAWLDER SEQ ID NO: 16 | 240 ± 40 nM |
| Influence of other amino acids on the shortened 9-mer peptide: | |
| 3 Asp: DVDAWLDER SEQ ID NO: 16 | 940 ± 140 nM |
| 3 Gly: DVGAWLDER SEQ ID NO: 16 | 570 ± 90 nM |
| 6 Phe: DVEAWFDER SEQ ID NO: 16 | not measurable |
| 6 Arg: DVEAWRDER SEQ ID NO: 16 | not measurable |
| 7 Gly: DVEAWLGER SEQ ID NO: 16 | 17 ± 4 nM |
| 8 Ala: DVEAWLDAR SEQ ID NO: 16 | 160 ± 30 nM |

A positive influence had in particular glycine at position 7 and alanine at position 8. Combination of these two amino acids:

Shortened peptide: DVEAWLGAR [SEQ ID NO: 16] 17±4 nM

Original peptide with Gly7: DVEAWLGERVPLVET [SEQ ID NO: 16] 4.2±0.7 nM

Original peptide: DVEAWLGARVPLVET [SEQ ID NO: 16] 4.1±0.6 nM

The original 15-mer peptide cannot further be improved. The shortened 9-mer peptide however can distinctly be improved by a glycine in lieu of the asparagic acid at position 7. The alanine in lieu of the glutamine acid at position 8 also has a slightly better binding affinity with regard to streptavidin. By the combination of these two amino acids the binding affinity cannot further be improved, however it will not become worse either.

The invention thus also comprises a 9-mer peptide with its not or only slightly conserved positions:

DVXAWLXXR (X=an arbitrary amino acid) [SEQ ID NO: 11]

Further, of course the shortened peptide with glycine at position 7:

DVEAWLGER [SEQ ID NO: 11]

and the shortened peptide with glycine at position 7 and alanine at position 8:

DVEAWLGAR [SEQ ID NO: 11]

Example 5

Variants of Sequences According to the Invention

In the following, particularly suited sequences according to the invention are given.

| SEQ ID NO: 1: | DVEAW |
| SEQ ID NO: 2: | DVEA |
| SEQ ID NO: 3: | VEAW |
| SEQ ID NO: 4: | DVE |
| SEQ ID NO: 5: | VEA |
| SEQ ID NO: 6: | EAW |
| SEQ ID NO: 7: | DVXAW |
| SEQ ID NO: 8: | DVXAWL |
| SEQ ID NO: 9: | DVXAWLX |
| SEQ ID NO: 10: | DVXAWLXX |
| SEQ ID NO: 11: | DVXAWLXXR |
| SEQ ID NO: 12: | DVXAWLXXRVPLVET |
| SEQ ID NO: 13: | VPLVET |

X at position 3 may be arbitrary, however in particular E, D or G. X at position 7 may be arbitrary, however in particular G or D. X at position 8 may be arbitrary, however in particular A or E. Sequence 13 is an optional carboxy-terminal extension of the sequence 11, and from sequence 13 1 to 6 amino acids may be connected, beginning amino-terminally.

---

The invention claimed is:

1. A purified streptavidin-binding peptide comprising or consisting of an amino acid sequence according to SEQ ID NO: 11, wherein X at position 3 is selected from the group consisting of glutamic acid, aspartic acid, and glycine.

* * * * *

SEQUENCE LISTING

<160> NUMBER OF SEQ ID NOS: 20

<210> SEQ ID NO 1
<211> LENGTH: 5
<212> TYPE: PRT
<213> ORGANISM: Artificial
<220> FEATURE:
<223> OTHER INFORMATION: binding peptide

<400> SEQUENCE: 1

Asp Val Glu Ala Trp
1               5

<210> SEQ ID NO 2
<211> LENGTH: 4
<212> TYPE: PRT
<213> ORGANISM: Artificial
<220> FEATURE:
<223> OTHER INFORMATION: binding peptide

<400> SEQUENCE: 2

Asp Val Glu Ala
1

<210> SEQ ID NO 3
<211> LENGTH: 4
<212> TYPE: PRT
<213> ORGANISM: Artificial
<220> FEATURE:
<223> OTHER INFORMATION: binding peptide

<400> SEQUENCE: 3

Val Glu Ala Trp
1

<210> SEQ ID NO 4
<211> LENGTH: 3
<212> TYPE: PRT
<213> ORGANISM: Artificial
<220> FEATURE:
<223> OTHER INFORMATION: binding peptide

<400> SEQUENCE: 4

Asp Val Glu
1

```
<210> SEQ ID NO 5
<211> LENGTH: 3
<212> TYPE: PRT
<213> ORGANISM: Artificial
<220> FEATURE:
<223> OTHER INFORMATION: binding peptide

<400> SEQUENCE: 5

Val Glu Ala
1

<210> SEQ ID NO 6
<211> LENGTH: 3
<212> TYPE: PRT
<213> ORGANISM: Artificial
<220> FEATURE:
<223> OTHER INFORMATION: binding peptide

<400> SEQUENCE: 6

Glu Ala Trp
1

<210> SEQ ID NO 7
<211> LENGTH: 5
<212> TYPE: PRT
<213> ORGANISM: Artificial
<220> FEATURE:
<223> OTHER INFORMATION: binding peptide
<220> FEATURE:
<221> NAME/KEY: misc_feature
<222> LOCATION: (3)..(3)
<223> OTHER INFORMATION: any aminoacid, in particular E, D, or G

<400> SEQUENCE: 7

Asp Val Xaa Ala Trp
1               5

<210> SEQ ID NO 8
<211> LENGTH: 6
<212> TYPE: PRT
<213> ORGANISM: Artificial
<220> FEATURE:
<223> OTHER INFORMATION: binding peptide
<220> FEATURE:
<221> NAME/KEY: misc_feature
<222> LOCATION: (3)..(3)
<223> OTHER INFORMATION: any aminoacid, in particular E, D or G

<400> SEQUENCE: 8

Asp Val Xaa Ala Trp Leu
1               5

<210> SEQ ID NO 9
<211> LENGTH: 7
<212> TYPE: PRT
<213> ORGANISM: Artificial
<220> FEATURE:
<223> OTHER INFORMATION: binding peptide
<220> FEATURE:
<221> NAME/KEY: misc_feature
<222> LOCATION: (3)..(3)
<223> OTHER INFORMATION: any aminoacid, in particular E, D or G
<220> FEATURE:
<221> NAME/KEY: misc_feature
<222> LOCATION: (7)..(7)
<223> OTHER INFORMATION: any aminoacid, in particular D or G

<400> SEQUENCE: 9

Asp Val Xaa Ala Trp Leu Xaa
1               5
```

```
<210> SEQ ID NO 10
<211> LENGTH: 8
<212> TYPE: PRT
<213> ORGANISM: Artificial
<220> FEATURE:
<223> OTHER INFORMATION: binding peptide
<220> FEATURE:
<221> NAME/KEY: misc_feature
<222> LOCATION: (3)..(3)
<223> OTHER INFORMATION: any aminoacid, in particular E, D or G
<220> FEATURE:
<221> NAME/KEY: misc_feature
<222> LOCATION: (7)..(7)
<223> OTHER INFORMATION: any aminoacid, in particular D or G
<220> FEATURE:
<221> NAME/KEY: misc_feature
<222> LOCATION: (8)..(8)
<223> OTHER INFORMATION: any aminoacid, in particular A or E

<400> SEQUENCE: 10

Asp Val Xaa Ala Trp Leu Xaa Xaa
1               5

<210> SEQ ID NO 11
<211> LENGTH: 9
<212> TYPE: PRT
<213> ORGANISM: Artificial
<220> FEATURE:
<223> OTHER INFORMATION: binding peptide
<220> FEATURE:
<221> NAME/KEY: misc_feature
<222> LOCATION: (3)..(3)
<223> OTHER INFORMATION: any aminoacid, in particular E, D, or G
<220> FEATURE:
<221> NAME/KEY: misc_feature
<222> LOCATION: (7)..(7)
<223> OTHER INFORMATION: any aminoacid, in particular D or G
<220> FEATURE:
<221> NAME/KEY: misc_feature
<222> LOCATION: (8)..(8)
<223> OTHER INFORMATION: any aminoacid, in particular A or E

<400> SEQUENCE: 11

Asp Val Xaa Ala Trp Leu Xaa Xaa Arg
1               5

<210> SEQ ID NO 12
<211> LENGTH: 15
<212> TYPE: PRT
<213> ORGANISM: Artificial
<220> FEATURE:
<223> OTHER INFORMATION: binding peptide
<220> FEATURE:
<221> NAME/KEY: misc_feature
<222> LOCATION: (3)..(3)
<223> OTHER INFORMATION: any aminoacid, in particular E, D or G
<220> FEATURE:
<221> NAME/KEY: misc_feature
<222> LOCATION: (7)..(7)
<223> OTHER INFORMATION: any aminoacid, in particular D or G
<220> FEATURE:
<221> NAME/KEY: misc_feature
<222> LOCATION: (8)..(8)
<223> OTHER INFORMATION: any aminoacid, in particular A or E

<400> SEQUENCE: 12

Asp Val Xaa Ala Trp Leu Xaa Xaa Arg Val Pro Leu Val Glu Thr
1               5                   10                  15

<210> SEQ ID NO 13
<211> LENGTH: 5
<212> TYPE: PRT
```

```
<213> ORGANISM: Artificial
<220> FEATURE:
<223> OTHER INFORMATION: binding peptide
<220> FEATURE:
<221> NAME/KEY: misc_feature
<222> LOCATION: (1)..(5)
<223> OTHER INFORMATION: sequence connected to the carboxy-terminal end
      of Seq.-ID 11, with 1 - 5 of said sequence, beginning
      amino-terminal

<400> SEQUENCE: 13

Pro Leu Val Glu Thr
1               5

<210> SEQ ID NO 14
<211> LENGTH: 15
<212> TYPE: PRT
<213> ORGANISM: Artificial
<220> FEATURE:
<223> OTHER INFORMATION: binding peptide

<400> SEQUENCE: 14

Asp Leu Tyr Asp Ile Asp Arg Asn Trp Val Gly His Pro Gln Gly
1               5                   10                  15

<210> SEQ ID NO 15
<211> LENGTH: 15
<212> TYPE: PRT
<213> ORGANISM: Artificial
<220> FEATURE:
<223> OTHER INFORMATION: binding peptide

<400> SEQUENCE: 15

Asp Asn Tyr Asp Ala Asp Leu Ala Trp Asp Thr His Pro Gln Asp
1               5                   10                  15

<210> SEQ ID NO 16
<211> LENGTH: 15
<212> TYPE: PRT
<213> ORGANISM: Artificial
<220> FEATURE:
<223> OTHER INFORMATION: binding peptide

<400> SEQUENCE: 16

Asp Val Glu Ala Trp Leu Asp Glu Arg Val Pro Leu Val Glu Thr
1               5                   10                  15

<210> SEQ ID NO 17
<211> LENGTH: 15
<212> TYPE: PRT
<213> ORGANISM: Artificial
<220> FEATURE:
<223> OTHER INFORMATION: binding peptide

<400> SEQUENCE: 17

Asp Val Glu Ala Trp Ile Ala Asp Pro Ala Val His Phe Thr Thr
1               5                   10                  15

<210> SEQ ID NO 18
<211> LENGTH: 9
<212> TYPE: PRT
<213> ORGANISM: Artificial
<220> FEATURE:
<223> OTHER INFORMATION: Streptag I

<400> SEQUENCE: 18

Ala Trp Arg His Pro Gln Phe Gly Gly
1               5
```

```
<210> SEQ ID NO 19
<211> LENGTH: 8
<212> TYPE: PRT
<213> ORGANISM: Artificial
<220> FEATURE:
<223> OTHER INFORMATION: Strep-tag II

<400> SEQUENCE: 19

Trp Ser His Pro Gln Phe Glu Lys
1               5

<210> SEQ ID NO 20
<211> LENGTH: 38
<212> TYPE: PRT
<213> ORGANISM: Artificial
<220> FEATURE:
<223> OTHER INFORMATION: SBP-tag

<400> SEQUENCE: 20

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35
```